United States Patent
Keogh et al.

(10) Patent No.: US 11,493,520 B2
(45) Date of Patent: Nov. 8, 2022

(54) ASSAYS FOR NUCLEOSOME REMODELING ACTIVITY

(71) Applicant: EpiCypher, Inc., Durham, NC (US)

(72) Inventors: Michael-Christopher Keogh, Cambridge, MA (US); Martis William Cowles, Chapel Hill, NC (US); Matthew Fruge Whelihan, Durham, NC (US)

(73) Assignee: EpiCypher, Inc., Durham, NC (US)

( * ) Notice: Subject to any disclaimer, the term of this patent is extended or adjusted under 35 U.S.C. 154(b) by 325 days.

(21) Appl. No.: 16/614,692

(22) PCT Filed: May 18, 2018

(86) PCT No.: PCT/US2018/033410
§ 371 (c)(1),
(2) Date: Nov. 18, 2019

(87) PCT Pub. No.: WO2018/213719
PCT Pub. Date: Nov. 22, 2018

(65) Prior Publication Data
US 2020/0200766 A1 Jun. 25, 2020

Related U.S. Application Data

(60) Provisional application No. 62/508,710, filed on May 19, 2017.

(51) Int. Cl.
*G01N 33/68* (2006.01)
*G01N 33/542* (2006.01)
*C12Q 1/48* (2006.01)

(52) U.S. Cl.
CPC .......... *G01N 33/6875* (2013.01); *C12Q 1/48* (2013.01); *G01N 33/542* (2013.01); *G01N 2500/00* (2013.01)

(58) Field of Classification Search
CPC ............ G01N 33/6875; G01N 33/542; G01N 2500/00; C12Q 1/48
See application file for complete search history.

(56) References Cited

U.S. PATENT DOCUMENTS

| 5,972,608 A | 10/1999 | Peterson et al. |
| 2015/0197801 A1* | 7/2015 | Muir .................. C40B 20/04 506/9 |

FOREIGN PATENT DOCUMENTS

WO 2013/184930 12/2013

OTHER PUBLICATIONS

Fry (Current Biology 2001 11:R185-R197). (Year: 2001).*
International Preliminary Report on Patentability corresponding to International Application No. PCT/US2018/033410 dated Nov. 28, 2019.
"Extended European Search Report corresponding to European Application No. 18802743.7 dated Jan. 22, 2021".
Al-Ani Gada, et al., "ISWI Remodels Nucleosomes through a Random Walk", Biochemistry 53(27):4346-4357 (Jun. 30, 2014).
Bunig, Ruth , et al., "Effect of Histone Acetylation on Nucleosome Dynamics Revealed by spFRET Microscopy", Biophysical Journal 96(3):55a (Feb. 1, 2009).
Goldman, Joseph A., et al., "Chromatin Remodeling by Imitation Switch (ISWI) Class ATP-dependent Remodeiers is Stimulated by Histone Variant H2A.Z", Journal of Biological Chemistry 285(7):4645-4651 (Feb. 12, 2010).
Luo, Yi , et al., "Single molecule fluorescence methodologies for investigating transcription factor binding kinetics to nucleosomes and DNA", Methods 70(2-3):108-118 (Oct. 7, 2014).
Hall et al. "Fluorescence polarization assays in high-throughput screening and drug discovery: a review", Methods Appl. Fluoresc. 4:1-20 (2016).
International Search Report and Written Opinion corresponding to International Application No. PCT/US2018/033410 dated Sep. 6, 2018.

* cited by examiner

*Primary Examiner* — Changhwa J Cheu
(74) *Attorney, Agent, or Firm* — Myers Bigel, P.A.

(57) ABSTRACT

The invention relates to assays for nucleosome remodeling activity using functionalized recombinant mononucleosomes. The functionalized recombinant mononucleosomes comprise a histone octamer comprising recombinant histone H2A, H2B, H3 and H4 proteins and a DNA template comprising a nucleosome positioning sequence that effectively positions the histone octamer and a signal site. The invention further relates to methods of using the assay to quantify enzymatic activity of remodeling enzymes and identifying modulators of remodeling enzyme activity.

21 Claims, 2 Drawing Sheets

ASSAYS FOR NUCLEOSOME REMODELING ACTIVITY

STATEMENT OF PRIORITY

This application is a 35 U.S.C. § 371 national phase application of PCT Application PCT/US2018/033410, filed on May 18, 2018, which claims the benefit of U.S. Provisional Application Ser. No. 62/508,710, filed on May 19, 2017, the entire contents of which are incorporated by reference herein.

FIELD OF THE INVENTION

The invention relates to assays for nucleosome remodeling activity using functionalized recombinant mononucleosomes. The invention further relates to methods of using the assay to quantify enzymatic activity of remodeling enzymes and identifying modulators of remodeling enzyme activity.

BACKGROUND OF THE INVENTION

Nucleosomes (Nucs) are the fundamental and repeating units of chromatin, comprised of a core histone octamer wrapped by ~147 bp DNA (Margueron et al., *Nature Rev. Genet.* 11(4):285 (2010)). Chromatin is more than a means to package the genome: it also regulates diverse cellular functions, including gene expression, chromosome transmission at mitosis, and DNA damage repair (Brown et al., *Hum. Mol. Genet*, 21(R1):R90 (2012); Lahtz et al., *J. Mol. Cell. Biol.* 3(1):51 (2011); Lunyak et al., *Hum. Mol. Genet.* 17(R1):R28 (2008); Reik, *Nature* 447(7143):425 (2007)). A key regulatory facet of these processes is mediated by nucleosome remodeling complexes that are recruited to specific genomic locations. ATP-dependent remodeling subunits then assemble, remodel, or eject nucleosomes to alter DNA accessibility for the transcription, replication and/or repair machineries. Defective nucleosome remodeling is associated with diverse human disorders including schizophrenia (McCarthy et al., *Mol. Psychiatry* 19(6):652 (2014)), cardiovascular disease (Bevilacqua et al., *Cardiovasc. Pathol.* 23(2):85 (2014)), intellectual disability (McCarthy et al., *Mol. Psychiatry* 19(6):652 (2014); Lopez et al., *Frontiers Behavioral Neurosci.* 9:100 (2015)) and cancer (Esteller, *N. Engl. J. Med.* 358:1148 (2008); Kumar et al., *Oncogene*, 35(34):4423 (2016); Sperlazza et al., *Blood* 126 (12):1462 (2015)). Therefore, nucleosome remodelers are compelling therapeutic targets (Mayes et al., *Adv. Cancer Res.* 121:183 (2014); Wu et al., *Oncotarget* 7(19):27158 (2016); Wang et al., *Clin. Cancer Res.* 20(1):21 (2014); Oike et al., *J Radiat. Res.* 55(4):613 (2014)).

SWI/SNF family chromatin remodeling complexes are of particular interest for targeted cancer treatment (Zinzalla, *Chembiochem.* 17(8):677 (2016); Helming et al., *Cancer Cell* 26(3):309 (2014); Hohmann et al., *Trends Genet.* 30(8): 356 (2014)). In the most extreme example, mutation in subunits from the SMARCA2/4 complexes are found in 20% of all human cancers, approaching the frequency of the most commonly mutated tumor suppressor, p53 (26%) (FIGS. 1A-1B) (Shain et al., *PLoS ONE* 8(1):e55119 (2013)). Mechanistically, cells containing SWI/SNF mutant complexes exhibit abnormal chromatin remodeling activity, leading to atypical gene expression that drives tumor initiation (Shain et al., *PLoS ONE* 8(1):e55119 (2013); Kadoch et al., *Nature Genet.* 45(6):592 (2013)). Furthermore, SWI/SNF-mutated cancers present currently unexploited vulnerabilities that make characterizing/inhibiting the complexes' chromatin remodeling activity especially appealing for drug discovery (Vangamudi et al., Cancer Res. 75 918 0; 3865 (2015); Wu et al., *Oncotarget* 7(19):27158 (2016); Helming et al., *Cancer Cell* 26(3):309 (2014)). Compromising the ATPase component (SMARCA2 or 4) in the mutated 'residual complexes' within cancer cells is sufficient to arrest growth/induce apoptosis while sparing normal cells with otherwise wild-type complexes (Helming et al., *Cancer Cell* 26(3):309 (2014)). This synthetic lethal relationship between SWI/SNF complex subunits may be exploited to target cancer cells while preserving healthy tissue. Therefore, inhibitors of nucleosome repositioning by SWI/SNF family complexes represent a promising opportunity to discover novel treatments for therapeutically challenging cancers.

Remodeling complexes make multivalent interactions with the DNA and histones in chromatin (see domains in FIG. 1A), which cannot be replicated with isolated oligonucleotide, peptide or histone substrates (Längst, *Genes* 6(3):299 (2015)). Furthermore, cell-derived nucleosome templates have highly heterogeneous epigenetic profiles, a feature that greatly complicates their use in biochemical studies, while in cell remodeling assays are often too complex to assign a definitive mechanism of action. By contrast, fully defined recombinant nucleosomes (rNucs; representing the full histone octamer wrapped in DNA) are ideal biochemical substrates as they provide users with a homogenous substrate population that can be synthetically modified for analysis via direct (and diverse) readouts, features that are essential to establish reliable assays for drug discovery (Allis, *Chembiochem.* 12(2):264 (2011); Fierz et al., *Nature Chem. Biol.* 8(5):417 (2012)).

Current techniques for quantifying rNuc repositioning include probing for cleaved DNA sequences with Southern blotting (Okada el al., *Mol. Cell. Biol.* 18(5):2455 (1998)), autoradiography and scintillation counting (Vicent et al., *Mol. Cell* 16(3):439 (2004)); primer extension by PCR (Trotter et al., Meth. Mol. Biol. 833:89 (2012)); or monitoring nucleosome repositioning (directly or after nuclease treatment) by differential migration on native PAGE (Carey et al., in Transcriptional Regulation in Eukaryotes: Concepts, Strategies, and Techniques, Cold Spring Harbor, Cold Spring Harbor Laboratory Press, 2009, pp. 539). However, these methods are slow, low-throughput and labor intensive, and thus not practical for screening large compound libraries (Chen et al., *J. Visualized Exp.* 92:51721 (2014); Byeon et al., *J. Biol. Chem.* 288(32):23182 (2013)).

There is a need in the art for improved nucleosome remodeling assays that are faster, more sensitive, and suitable for high-throughput assays.

SUMMARY OF THE INVENTION

The present invention relates to no-wash, high-throughput nucleosome remodeling assays. At the core of this invention is the functionalization of recombinant fully defined mononucleosomes to enable single pot, no-wash remodeling assays for the rapid quantification of enzyme activity. Further, these functionalized mononucleosomes can be chemically modified to carry specific histone post-translational modifications (PTMs), such as acetylation, methylation, phosphorylation, ubiquitination, etc. These specialized nucleosome substrates can be used in assays to study how compounds or specific histone PTMs modulate (inhibit or activate) enzyme activity. See FIG. 2 for examples of how nucleosomes can be functionalized for various assay readouts.

Thus, one aspect of the invention relates to a functionalized recombinant mononucleosome comprising:
(a) a histone octamer comprising recombinant histone H2A, 1H2B, H3 and H4 proteins (with or without PTMs or replacement histone variants); and
(b) a DNA template comprising a nucleosome positioning sequence (NPS) that effectively positions the histone octamer and a signal site.

Another aspect of the invention relates to a method for quantifying enzymatic activity of a remodeling enzyme, comprising:
(a) contacting the functionalized recombinant mononucleosome of the invention with a remodeling enzyme; and
(b) measuring a signal from the signal site;
thereby quantifying the enzymatic activity of the remodeling enzyme.

A further aspect of the invention relates to a method for identifying a compound that modulates remodeling enzyme activity, comprising:
(a) contacting the functionalized recombinant mononucleosome of the invention with a remodeling enzyme in the presence and absence of a compound; and
(b) measuring a signal from the signal site in the presence and absence of the compound;
wherein a difference in the signal in the presence and absence of the compound identifies the compound as one that modulates remodeling enzyme activity.

These and other aspects of the invention are set forth in more detail in the description of the invention below.

DETAILED DESCRIPTION OF THE INVENTION

Figures 1A, 1B:
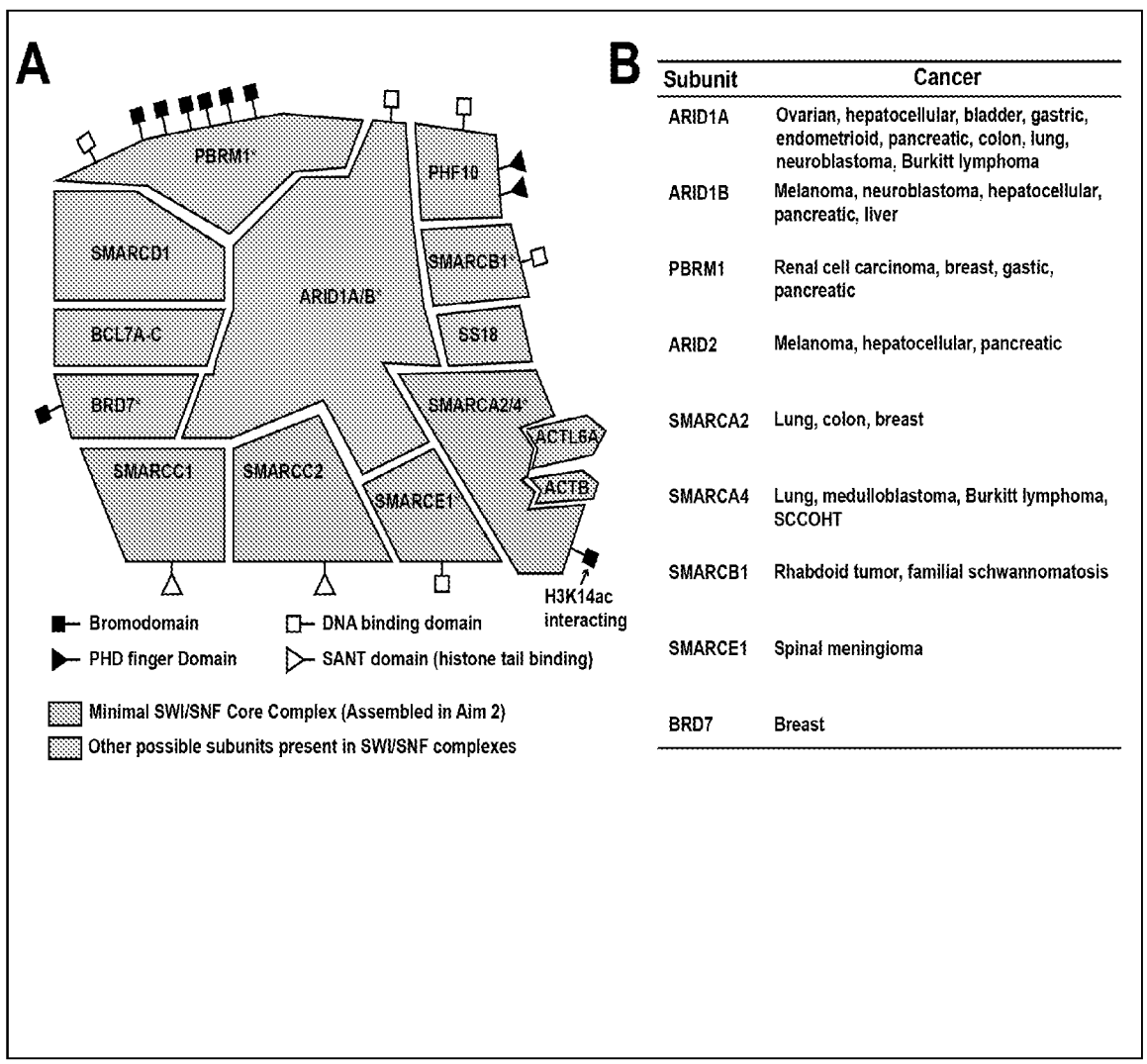
FIG. 1A shows a schematic of SWI/SNF remodeling complex. The subunits SMARCC1, SMARCC2, SMARCE1, and SMARCA2/4 make up the minimal core that recapitulates activity of full complex.
FIG. 1B shows a list of cancers associated with various SWI/SNF subunit mutations. Asterisks in A indicate associated cancers in B. SMARCA2 and SMARCA4 both contain a bromodomain that specifically interacts with H3K14ac.
Figures 2A, 2B:
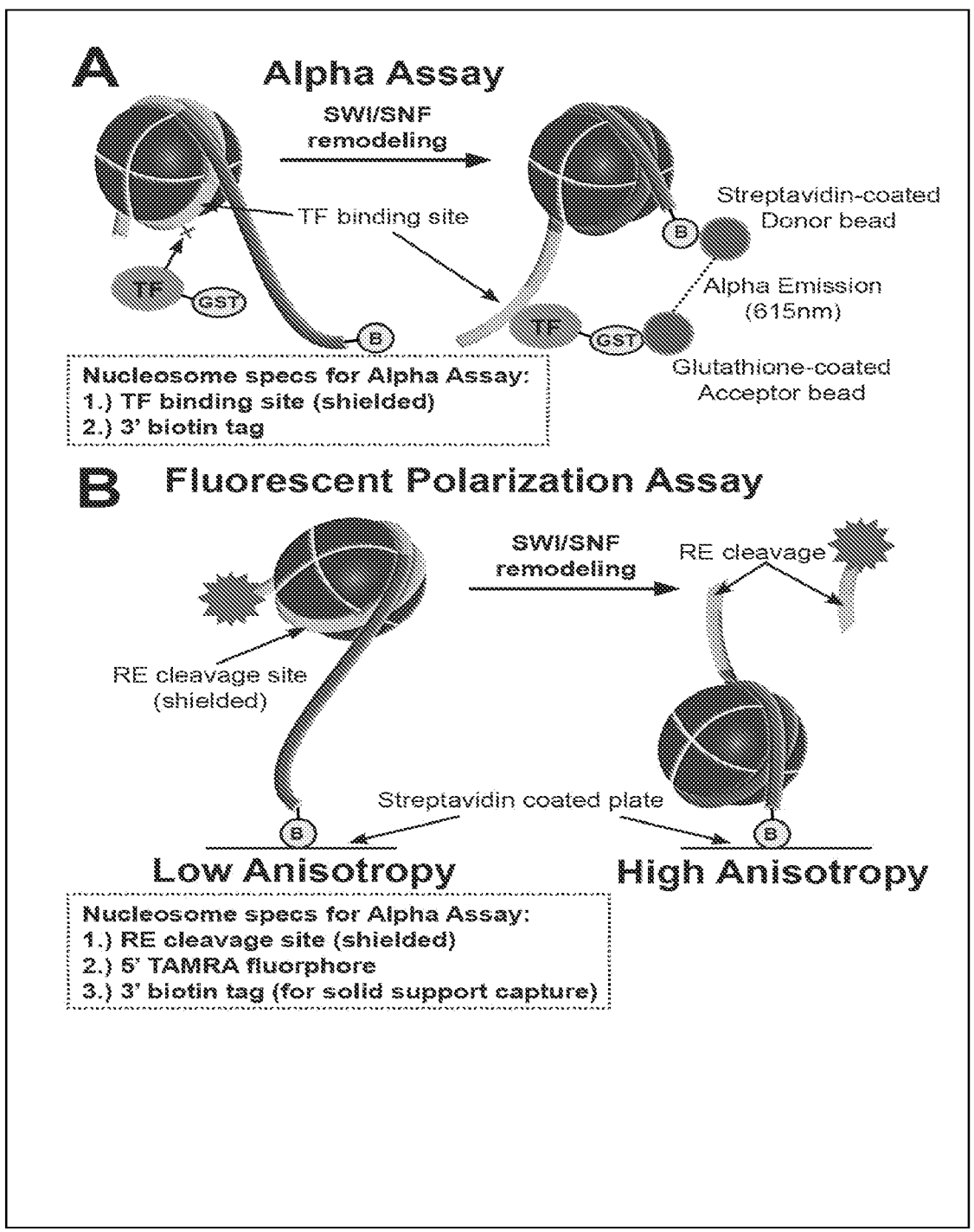
FIGS. 2A-2B show cartoon schematics of amplified luminescent proximity homogenous assay (ALPHA) (A) and fluorescence polarization (FP) (B) assay design. Alpha design uses a GST-fused transcription factor (TF), which is only able to bind following nucleosome remodeling. FP design leverages restriction enzyme accessibility (for example to GATC), but monitors activity via anisotropy vs. DAM radiolabeling.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of nucleosomes, and transiently and stably transfected cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

I. Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid or protein means that the nucleic acid or protein does not contain any element other than the recited element(s) that significantly alters (e.g., more than about 1%, 5% or 10%) the function of interest of the nucleic acid or protein.

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By "substantially retain" a property, it is meant that at least about 75%, 85%, 90%, 95%, 97%, 98%, 99% or 100% of the property (e.g., activity or other measurable characteristic) is retained.

II. Functionalized Recombinant Mononucleosomes

The present invention provides improved assays for nucleosome remodeling activity that utilize functionalized recombinant mononucleosomes. The recombinant mononucleosomes may comprise a mix of recombinant and/or synthetic histone octamers, one or more of which may comprise PTMs. The recombinant mononucleosomes used as substrates in the present assays advantageously are homogenous and have a defined PTM status. Previous assays, such as those described in U.S. Pat. No. 5,972,608, use cell-derived octamers, which are heterogeneous and have undefined histone PTMs. U.S. Pat. No. 5,972,608 describes the use of nucleosome arrays, comprising synthetically derived DNA with linked repeats and multiple octamers, as the substrate. This substrate provides high background signals due to the presence of naked DNA that is not part of a nucleosome. The assay described therein is a low throughput assay utilizing a gel-based readout. In contrast, the present invention advantageously is suitable for high throughput screening as it utilizes a no-wash, single pot assay.

Thus, one aspect of the present invention relates to a functionalized recombinant mononucleosome comprising:
(a) a histone octamer comprising recombinant histone H2A, H2B, H3 and H4 proteins; and
(b) a DNA template comprising a nucleosome positioning sequence (NIPS) that effectively positions the histone octamer and a signal site.

The histones in the mononucleosomes may contain all recombinant or synthetic histones having naturally occurring sequences. In some embodiments, the mononucleosomes may comprise one or more of the histones that are synthetic or naturally-occurring histone variants, such as H2A.X or H3.3. The variants may be a supplement, a mixture, and/or a replacement for one or more of the histones with naturally occurring sequences.

In some embodiments, one or more of the histones comprises at least one PTM. A single histone may comprise 1 or more PTMs, e.g., 1, 2, 3, 4, 5, or more and the mononucleosome may comprise 1 or more PTMs, e.g., 1, 2, 3, 4, 5, or more. PTMs include, for example, lysine methylation, serine phosphorylation, arginine methylation, lysine acylation (e.g., acetylation, crotonylation, butyrylation), lysine ubiquitylation, etc. PTMs may be incorporated into histones by methods known in the art, including without limitation, native chemical ligation, amber suppression, maleimide linkage, or enzymatic methods.

The DNA template may comprises an acceptor sequence located 5' or 3' of the NPS to contain a re-positioned nucleosome after ATPase activity. In some embodiments, the acceptor sequence is 10-1000 basepairs in length.

The signal site on the DNA template is designed to provide an assay readout and may be selected based on the type of assay being performed. Suitable assay types include, without limitation, an amplified luminescent proximity homogenous assay (ALPHA), fluorescence polarization (FP), or time-resolved fluorescence resonance energy transfer (TR-FRET) assay.

In some embodiments, the signal site is a protein interaction site that is shielded in the functionalized recombinant mononucleosome. Remodeling enzyme activity may remove the shield allowing the site to be accessed and a signal to be detected. In certain embodiments, the protein interaction site is a restriction enzyme site or other nuclease recognition site. In certain embodiments, the protein interaction site is a transcription factor binding site or chaperone binding site. In some embodiments, the signal site is a fluorophore, such as FAM or TAMRA.

The DNA template may further comprise a functional tag that is useful in the assay, e.g., to immobilize the mononucleosome on a surface, e.g., an assay plate or well. The functional tag may be, for example, one half of a binding pair, such as biotin or digoxigenin. The other half of the binding pair may be bound to the surface on which the mononucleosome will be immobilized.

While the description above is based on functionalized recombinant mononucleosomes, the invention contemplates functionalized recombinant nucleosomes comprising 2 or more histone octamers, e.g., 2, 3, 4, or 5 histone octamers, and 1 or more than 1 DNA template. In some embodiments, the functionalized recombinant nucleosomes comprise less than 6, 5, 4, or 3 histone octamers. In some embodiments, each histone octamer comprises the same PTM(s), e.g., the nucleosomes are homogenous.

III. Assay Methods

The functionalized recombinant mononucleosomes may be used as a substrate in any assay for which nucleosomes are useful. In one aspect, the mononucleosomes may be used in a method for quantifying enzymatic activity of a remodeling enzyme. In another aspect the mononucleosomes may be used in a screening method for identifying compounds that are modulators of remodeling enzyme activity, e.g., a high-throughput screening assay.

Thus, one aspect of the invention relates to a method for quantifying enzymatic activity of a remodeling enzyme, comprising:
(a) contacting the functionalized recombinant mononucleosome of the invention with a remodeling enzyme; and
(b) measuring a signal from the signal site;
thereby quantifying the enzymatic activity of the remodeling enzyme.

The assay may further comprise a negative control, e.g., in the absence of remodeling enzyme, for a relative comparison of enzyme activity.

In some embodiments, the assay is carried out on a surface, e.g., in an assay plate or well. In some embodiments, the functionalized recombinant mononucleosome is immobilized on a surface, e.g., through the presence of one half of a binding pair (such as biotin) on the DNA template or one or more histones and the other half of the binding pair (such as streptavidin) on the surface.

The format of the assay may be any type of assay known in the art for which a suitable signal generator may be incorporated into the mononucleosome, e.g., into the DNA template. Suitable assay types include, without limitation, an ALPHA, FP, or TR-FRET assay.

In one embodiment, the assay is a FP assay, wherein the DNA template comprises a restriction enzyme site or other nuclease recognition site and a fluorophore; the functionalized recombinant mononucleosome is contacted with the remodeling enzyme and the restriction enzyme or other nuclease; and the enzymatic activity is quantified by measuring relative changes in anisotropy.

In one embodiment, the assay is an ALPHA FP assay, wherein the DNA template comprises a protein interaction site; and the assay comprises the steps of:
(a) contacting the functionalized recombinant mononucleosome with the remodeling enzyme; and
(b) contacting the functionalized recombinant mononucleosome with an epitope-tagged protein that binds the protein interaction site, beads comprising an ALPHA acceptor, and beads comprising an anti-epitope tag and an ALPHA donor;
and the enzymatic activity is quantified by measuring changes in ALPHA signal.

In certain embodiments, the DNA template comprises the first half of a binding part (such as biotin) and the beads comprising an ALPHA acceptor are coated with the second half of the binding pair (such as streptavidin).

The epitope tag on the protein may be any suitable tag, such as glutathione, and the anti-epitope tag may be an antibody or a fragment thereof.

In one embodiment, the assay is a TR-FRET assay, wherein the DNA template comprises a fluorophore; the mononucleosome comprises a histone conjugated to a fluorophore or quencher molecule; and the enzymatic activity is quantified by measuring changes in FRET.

In any of the methods, the remodeling enzyme may be selected from any family of remodeling complexes, e.g., SWI/SNF, ISWI, NuRD/Mi-s/CDH, INO80, SWR1, and any combination thereof.

Another aspect of the invention relates to a method for identifying a compound that modulates remodeling enzyme activity, comprising:
(a) contacting the functionalized recombinant mononucleosome of the invention with a remodeling enzyme in the presence and absence of a compound; and
(b) measuring a signal from the signal site in the presence and absence of the compound;
wherein a difference in the signal in the presence and absence of the compound identifies the compound as one that modulates remodeling enzyme activity.

In some embodiments, the assay is carried out on a surface, e.g., in an assay plate or well. In some embodiments, the functionalized recombinant mononucleosome is immobilized on a surface, e.g., through the presence of one half of a binding pair (such as biotin) on the DNA template or one or more histones and the other half of the binding pair (such as streptavidin) on the surface.

The format of the assay may be any type of assay known in the art for which a suitable signal generator may be incorporated into the mononucleosome, e.g., into the DNA template. Suitable assay types include, without limitation, an ALPHA, FP, or TR-FRET assay.

In one embodiment, the assay is a FP assay, wherein the DNA template comprises a restriction enzyme site or other nuclease recognition site and a fluorophore; the functionalized recombinant mononucleosome is contacted with the remodeling enzyme and the restriction enzyme or other nuclease in the presence and absence of the compound; and the enzymatic activity is quantified by measuring relative changes in anisotropy.

In one embodiment, the assay is an ALPHA FP assay, wherein the DNA template comprises a protein interaction site; and the assay comprises the steps of:
(a) contacting the functionalized recombinant mononucleosome with the remodeling enzyme in the presence and absence of the compound; and
(b) contacting the functionalized recombinant mononucleosome with an epitope-tagged protein that binds the protein interaction site, beads comprising an ALPHA acceptor, and beads comprising an anti-epitope tag and an ALPHA donor;
and the enzymatic activity is quantified by measuring changes in ALPHA signal.

In certain embodiments, the DNA template comprises the first half of a binding part (such as biotin) and the beads comprising an ALPHA acceptor are coated with the second half of the binding pair (such as streptavidin).

The epitope tag on the protein may be any suitable tag, such as glutathione, and the anti-epitope tag may be an antibody or a fragment thereof.

In one embodiment, the assay is a TR-FRET assay, wherein the DNA template comprises a fluorophore; the mononucleosome comprises a histone conjugated to a fluorophore or quencher molecule; and the enzymatic activity is quantified by measuring changes in FRET.

In any of the methods, the remodeling enzyme may be selected from any family of remodeling complexes, e.g., SWI/SNF, ISWI, NuRD/Mi-s/CDH, INO80, SWR1, and any combination thereof.

The foregoing is illustrative of the present invention, and is not to be construed as limiting thereof. The invention is defined by the following claims, with equivalents of the claims to be included therein.

We claim:

1. A functionalized recombinant mononucleosome comprising:
   (a) a histone octamer comprising recombinant historic H2A, H2B, H3 and H4 proteins; and
   (b) a DNA template comprising a nucleosome positioning sequence (NPS) that effectively positions the histone octamer and a signal site;
   wherein the signal site is a protein interaction site that is shielded in the functionalized recombinant mononucleosome;
   wherein the protein interaction site is a restriction enzyme site or other nuclease recognition site; and
   wherein the protein interaction site is not a transcription factor binding site.

2. The functionalized recombinant mononucleosome of claim 1, wherein one or more of the histories is a synthetic or naturally-occurring histone variant.

3. The functionalized recombinant mononucleosome of claim 1, wherein one or more of the histones comprises one or more post-translational modification (PTM).

4. The functionalized recombinant mononucleosome of claim 2, wherein one or more of the histones or histone variants comprises one or more PTMs.

5. The functionalized recombinant mononucleosome of claim 1, wherein the DNA template comprises an acceptor sequence located 5' or 3' of the NPS.

6. The functionalized recombinant mononucleosome of claim 5, wherein the acceptor sequence is 10-1000 basepairs.

7. The functionalized recombinant mononucleosome of claim 1, wherein the protein interaction site is a chaperone binding site.

8. The functionalized recombinant mononucleosome of claim 1, wherein the mononucleosome comprises a functional tag.

9. A method for quantifying enzymatic activity of a remodeling enzyme, comprising:
   (a) contacting the functionalized recombinant mononucleosome of claim 1 with the remodeling enzyme and a restriction enzyme or other nuclease that interacts with the signal site; and
   (b) measuring a signal from the signal site;
   thereby quantifying the enzymatic activity of the remodeling enzyme.

10. The method of claim 9, further comprising measuring a signal from the signal site of a negative control.

11. The method of claim 9, wherein the functionalized recombinant mononucleosome is immobilized on a surface.

12. The method of claim 11, wherein the DNA template comprises biotin and the surface comprises streptavidin.

13. The method of claim 9, which is a fluorescence polarization (FP) assay,
   wherein the DNA template comprises a restriction enzyme site or other nuclease recognition site and a fluorophore;
   the functionalized recombinant mononucleosome is contacted with the remodeling enzyme and the restriction enzyme or other nuclease;
   and the enzymatic activity is quantified by measuring relative changes in anisotropy.

14. The method of claim 9, which is a time-resolved fluorescence resonance energy transfer (TR-FRET) assay,
   wherein the DNA template comprises a fluorophore;
   the mononucleosome comprises a histone conjugated to a fluorophore or quencher molecule;
   and the enzymatic activity is quantified by measuring changes in FRET.

15. The method of claim 9, wherein the remodeling enzyme is selected from Switch/Sugar Non-fermentable (SWI/SNF), Imitation Switch (ISWI), Nucleosome Remodeling Deacetylase (NuRD)/Mi-2/Chromodomain Helicase DNA Binding (CDH), inositol autotrophy 80 (INO80), Swi2/Snf2 related 1 (SWR1), and any combination thereof.

16. A method for identifying a compound that modulates remodeling enzyme activity, comprising:
   (a) contacting the functionalized recombinant mononucleosome of claim 1 with the remodeling enzyme and a restriction enzyme or other nuclease that interacts with the signal site; in the presence and absence of the compound; and
   (b) measuring a signal from the signal site in the presence and absence of the compound;
   wherein a difference in the signal in the presence and absence of the compound identifies the compound as one that modulates the remodeling enzyme activity.

17. The method of claim 16, wherein the functionalized recombinant mononucleosome is immobilized on a surface.

18. The method of claim 17, wherein the DNA template comprises biotin and the surface comprises streptavidin.

19. The method of claim 16 which is a FP assay,
   wherein the DNA template comprises a restriction enzyme site or other nuclease recognition site and a fluorophore;
   the functionalized recombinant mononucleosome is contacted with the remodeling enzyme and the restriction enzyme or other nuclease in the presence and absence of the compound;
   and the enzymatic activity is quantified by measuring relative changes in anisotropy.

20. The method of claim 16 which is a TR-FRET assay,
   wherein the DNA template comprises a fluorophore;
   the mononucleosome comprises a histone conjugated to a fluorophore or quencher molecule;
   and the enzymatic activity is quantified by measuring changes in FRET.

21. The method of claim 16, wherein the remodeling enzyme is selected from Switch Sugar Non-fermentable (SWI/SNF), Imitation Switch (ISWI), Nucleosome Remodeling Deacetylase (NuRD)/Mi-2/Chromodomain Helicase DNA Binding (CDH), inositol auxotrophy 80 (INO80), Swi2/Snf2 related 1 (SWR1), and any combination thereof.

\* \* \* \* \*

UNITED STATES PATENT AND TRADEMARK OFFICE
CERTIFICATE OF CORRECTION

PATENT NO. : 11,493,520 B2
APPLICATION NO. : 16/614692
DATED : November 8, 2022
INVENTOR(S) : Keogh et al.

Page 1 of 1

It is certified that error appears in the above-identified patent and that said Letters Patent is hereby corrected as shown below:

On the Title Page

Item [56], Column 2, Goldman cite: Please correct "ATP-dependent Remodeiers" to read --ATP-dependent Remodelers--

In the Claims

Column 8, Line 53, Claim 1: Please correct "historic" to read --histone--

Column 8, Line 66, Claim 2: Please correct "histories" to read --histones--

Column 9, Line 2, Claim 3: Please correct "histories" to read --histones--

Column 10, Line 43, Claim 21: Please correct "Switch Sugar" to read --Switch/Sugar--

Signed and Sealed this
Twenty-eighth Day of February, 2023

Katherine Kelly Vidal
*Director of the United States Patent and Trademark Office*